United States Patent [19]

Typpo

[11] 4,247,205
[45] Jan. 27, 1981

[54] GAS MEASURING APPARATUS WITH STANDARDIZATION MEANS, AND METHOD THEREFOR

[75] Inventor: Pekka M. Typpo, Cupertino, Calif.

[73] Assignee: Measurex Corporation, Cupertino, Calif.

[21] Appl. No.: 8,865

[22] Filed: Feb. 2, 1979

[51] Int. Cl.³ .............. G01N 21/25; G01N 21/59; G01N 21/85
[52] U.S. Cl. .............. 356/438; 250/573; 356/407; 356/440
[58] Field of Search .............. 356/437, 438, 439, 440, 356/407; 250/573

[56] References Cited

U.S. PATENT DOCUMENTS 2,498,506  2/1950  Ramser .............. 356/439
3,895,233  7/1975  Boll et al. .............. 356/437

FOREIGN PATENT DOCUMENTS 2430672  1/1976  Fed. Rep. of Germany .............. 356/440

Primary Examiner—Vincent P. McGraw
Attorney, Agent, or Firm—Ronald L. Yin

[57] ABSTRACT

An apparatus and a method for standardizing a gas measuring device has a source capable of emitting a beam of radiation aligned to impinge a detector and gas particles. A hollow, open-ended tube is used as a standardization means and is placed adjacent to the beam. The tube can be moved to enclose the beam, to prevent the gas from intercepting the beam, and to transmit substantially all of the radiation from the source to the detector.

7 Claims, 5 Drawing Figures

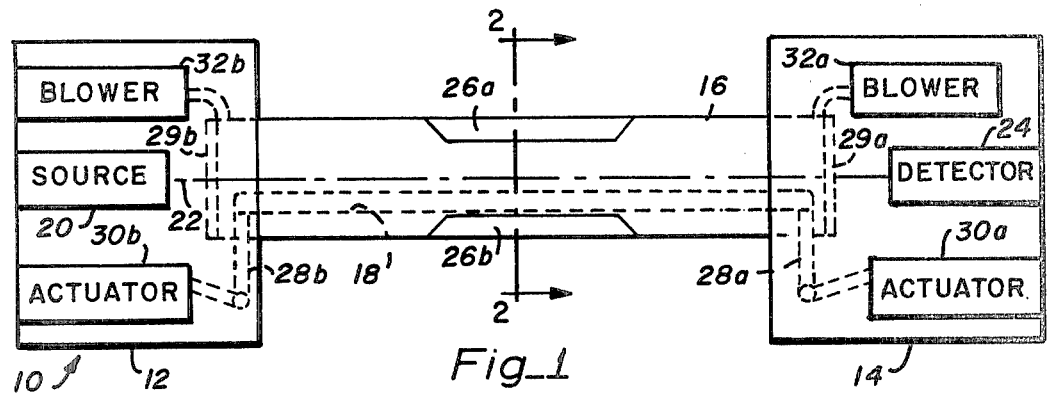
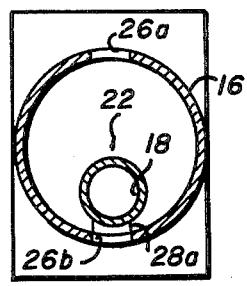
Fig_2A
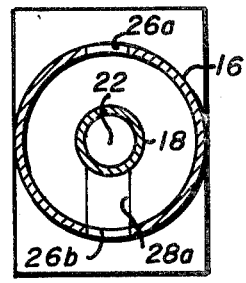
Fig_2B
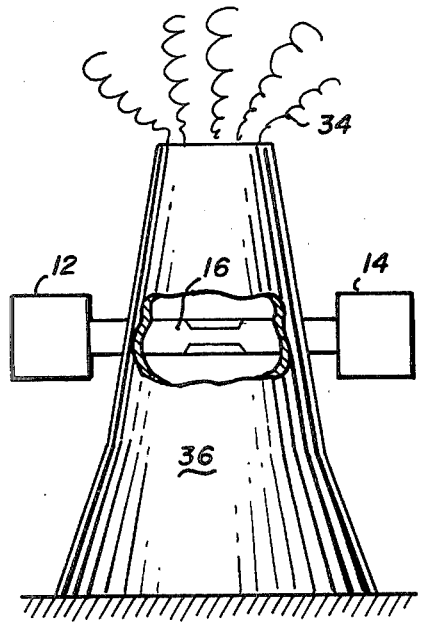
Fig_3
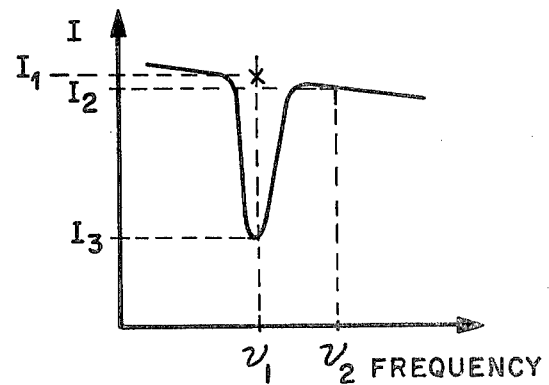
Fig_4

GAS MEASURING APPARATUS WITH STANDARDIZATION MEANS, AND METHOD THEREFOR

BACKGROUND OF THE INVENTION

1. Field of Invention

The present invention relates to an apparatus and a method for measuring the amount of gas. The present invention also relates to a standardization means for such a gas measuring device. Typically, these gases are the exhaust gases, emitted through stacks, produced as a result of combustion.

2. Prior Art

Gas measuring apparatus for monitoring the output of combustion at the stack is well known, see for example U.S. Pat. No. 4,076,425. Typically, these devices operate in harsh environments and in locations that are not easily accessible. Some of the problems, caused thereby, are: lamp aging, drift in electronics and dirt build-up on the window. Thus, to operate effectively, i.e. maintain accuracy and repeatability, these devices must have self-contained standardization means.

Heretofore, one standardization means is described in U.S. Pat. No. 3,836,237. That reference teaches, inter alia, the use of air curtains to keep windows clean. However, despite this practice of air curtains, dirt does build up on the window and must be accounted for in the standardization process. U.S. Pat. Nos. 3,838,925 and 4,076,425 teach the use of alternative optical paths to correct for lamp aging and drift in electronics. These references, however, do not teach the correction of other factors, such as dirt on the windows.

U.S. Patent Application Ser. Nos. 919,442 and 919,237 both filed on June 26, 1978, describe standardization means in gas measuring apparatus. However, those disclosures teach housing means with openings and means to close those openings and to purge gas from the housing means. These are cumbersome additions to the apparatus.

SUMMARY OF THE INVENTION

An apparatus for measuring select properties of gas particles comprises a source capable of emitting a beam of radiation. The beam is aligned to impinge a detector and the gas particles. A standardization means is adjacent to the beam, and is capable of being moved to enclose the beam, to prevent the gas particles from intercepting the beam and to transmit substantially all of the radiation from the source to the detector.

A method of using such a gas measuring apparatus comprises emitting said beam of radiation impinging the gas particles. The amount of radiation received by the detector is measured. The standardization means is moved to enclose the beam. The amount of radiation received by the detector is determined. The amount of gas particles is calculated based upon the amount of radiation measured and the amount of radiation determined.

BRIEF DESCRIPTION OF THE DRAWINGS

FIG. 1 is a side view of the gas measuring apparatus of the present invention.

FIG. 2A is a cross-sectional view of FIG. 1 taken along the plane 2—2, showing the apparatus of the present invention with the standardization means to one side of the beam of radiation.

FIG. 2B is a cross-sectional view of FIG. 1 taken along the plane 2—2, showing the apparatus of the present invention with the standardization means in place.

FIG. 3 is a pictorial view of the use of the apparatus of the present invention in a stack to monitor the exhaust gas from the combustion.

FIG. 4 is a graph of the absorption spectrum of a typical gas as a function of the frequency.

DETAILED DESCRIPTION OF THE DRAWINGS

Referring to FIG. 1 there is shown a gas measuring apparatus 10 of the present invention. The gas measuring apparatus 10 comprises a first enclosure 12, a second enclosure 14 and a first tube 16. The first tube 16 is hollow inside. The first enclosure 12 is to one side of the first tube 16 while the second enclosure 14 is to the other side of the first tube 16. Within the first tube 16 is a second tube 18. The second tube 18 is also hollow inside. A source 20 is in the first enclosure 12. The source 20 is capable of emitting a beam 22 of radiation (shown as dash-dot-dash line). The beam 22 is aligned, to pass through inside the first tube 16, and to impinge a detector 24 in the second enclosure 14. The first tube 16 encloses the beam 22. The first tube 16 has a plurality of apertures (only 26a and 26b are shown). The apertures 26a and 26b are located on opposite sides of the first tube 16; they permit gas to enter the first tube 16 via one aperture, e.g. 26b, to intercept the beam 22, and to exit via another aperture, e.g. 26a. The second tube 18 is positioned adjacent to the beam 22 (shown in FIG. 2A) and is capable of being moved to enclose the beam 22 (shown in FIG. 2B). The second tube 18, when moved into the position shown in FIG. 2B, i.e. to a position enclosing the beam 22, displaces the gas particles intercepted by the beam 22; prevents further gas particles from entering the second tube 18 to intercept the beam 22; and transmits substantially all of the radiation from the source 20 to the detector 24. The movement of the second tube 18 is accomplished by actuators 30a and 30b moving levers 28a and 28b which are attached to both sides of the second tube 18. Blowers 32a and 32b are provided to confine the gas substantially within the region of the apertures 26a and 26b of the first tube 16 and to minimize dirt build-up on the windows 29a and 29b, which are located on the ends of the first tube 16.

One use of the apparatus 10 of the present invention is in monitoring the exhaust gas 34 of combustion from a stack 36, shown in FIG. 3. Typically, the first enclosure 12 and the second enclosure 14 are on opposite sides of the stack 36, with the first tube 16 passing through the stack 36. In such application, the apparatus 10 is useful for monitoring the exhaust gas 34 to insure compliance with applicable environmental standards, such as the EPA. In such application, the apparatus 10 may operate as an opacity sensor, with the source 20 emitting a beam 22 of visible light.

In general, the first tube 16 is needed only to provide structural support for the apparatus 10. Thus, for example, if in FIG. 3, the first enclosure 12 and second enclosure 14 could be structurally attached to the side of the stack 36, the first tube 16 would not be needed. The heart of the invention is the second tube 18 and its ability to move to enclose the beam 22 and to prevent the gas particles 34 from intercepting the beam 22. In the preferred embodiment, the second tube 18 is simply a round tube open at both ends. The open ends permit the transmittance of substantially all of the radiation from the source 20 to the detector 24. The second tube 18 contains gas, such as ambient air, which does not contain any gas particles 34 under investigation emitted from the stack 36. Since the second tube 18 is nearly as long as the first tube 16, the length of the second tube 18, and its proximity to the blowers 32a and 32b, would preclude gas particles 34 from entering inside the second tube 18.

In the method of the present invention, the source 20 emits a beam 22 of radiation at a frequency (shown as $\nu_1$ in FIG. 4) which is absorbed by the gas 34. The beam 22 passes through the gas 34 and is absorbed as it travels to the detector 24. The intensity of the beam 22, received by the detector 24, is dependent upon the amount of absorption, i.e. the greater the absorption, the lower the intensity of the beam 22 received by the detector 24, and vice versa. This is shown as $I_3$ in FIG. 4. The second tube 18 is then moved to enclose the beam 22. The detector 24 measures the radiation after the beam 22 passes through the second tube 18, unimpeded by the gas 34. This is shown as $I_1$ in FIG. 4. The amount of gas 34 that was detected by the detector 24, prior to the second tube 18 being moved, is calculated based upon $I_1$ and $I_3$ in accordance with Beer's law, i.e.

$$I_3 = I_1 e^{-\mu c L} \text{ or } c = (1/\mu L) Ln(I_1/I_3)$$

where
$\mu$—absorption coefficient $$( \frac{1}{ppm - cm} )$$

c—concentration of gas (ppm)
L—path length in gas (cm)

Typically, the frequency $\nu_1$ is in the infrared region and the curve shown in FIG. 4 is the absorption band of carbon dioxide. The advantage of the apparatus and method of the present invention is that the reference measurement (i.e. the measurement made without absorption by the gas 34) is performed under substantially the same condition as the measurement with the gas 34. Except for the removal of the gas 34 the reference measurement uses the same source and electronics, follows the same optical path and is subject to the same environment as the measurement made with the gas 34. This provides for greater accuracy and reliability than has been achieved heretofore.

Heretofore, because it has not been possible to make a measurement with the gas 34 and a measurement without the gas 34, measurements were made based upon a beam of radiation at two different frequencies—one which is absorbed by the gas 34 and another which is not absorbed. In the method of the prior art, the source 20 emits a beam 22 of radiation at a first frequency $\nu_1$ which is absorbed by the gas 34 and a second frequency $\nu_2$ which is not absorbed by the gas 34. The detector 24 receives the beam 22 after it passes through the gas 34. The detector 24 measures the amount of first frequency $\nu_1$ received, i.e. $I_3$, and measures the amount of second frequency $\nu_2$ received, i.e. $I_2$. Calculation of the amount of gas 34 is made based upon $I_2$ and $I_3$ in accordance with Beer's law, based upon the assumption that $I_2$ is the same as $I_1$. However, it should be noted from FIG. 4, that even though the second frequency $\nu_2$ is chosen such that it is not absorbed by the gas 34, the amount of second frequency $\nu_2$ received may not be exactly the same as the amount of first frequency $\nu_1$ received but without the gas 34, i.e. $I_2$ may not necessarily be exactly the same as $I_1$. There are many possible causes for this, including drift in electronics, since $\nu_2$ is a frequency different from $\nu_1$. This is clearly a source of error.

In another method of the present invention, this error is eliminated by standardizing the value of $I_2$, i.e. determining the quantitative relationship between $I_2$ and $I_1$. To standardize the value of $I_2$, the second tube 18 is moved to enclose the beam 22. The source 20 emits a beam of radiation at a first frequency $\nu_1$ which would have been absorbed by the gas 34 and a second frequency $\nu_2$ which is not absorbed by the gas 34. The detector 24 measures the amount of radiation received at first frequency $\nu_1$ (i.e. $I_1$) and the amount of radiation received at second frequency $\nu_2$ (i.e. $I_2$). A standardization factor based upon $I_1$ and $I_2$ is determined, i.e.

$$K = I_1/I_2$$

Thereafter, in the measurement of the amount of gas 34 using a first frequency $\nu_1$ and a second frequency $\nu_2$, the calculation of the amount of gas 34 is based upon $I_3$, $I_2$ and K in accordance with $$I_3 = K I_2 e^{-\mu c L} \text{ or } c = (1/\mu L) Ln(K I_2/I_3)$$

where $\mu$, c and L are as previously discussed. In this method, the second tube 18 need not be moved upon every measurement. Instead, the movement of the second tube 18 is used to standardize the apparatus 10 and to correlate $I_2$ to $I_1$.

What is claimed is:

1. A gas measuring apparatus, capable of measuring select properties of gas particles, with standardization means, comprising:
   a source, capable of emitting a beam of radiation;
   a detector;
   said beam aligned to impinge said detector, and aligned to impinge said gas particles;
   a standardization means substantially hollow and tubular in shape, positioned immediately adjacent to said beam;
   said means capable of being moved in a direction substantially perpendicular to said beam to enclose said beam, to prevent said gas particles from intercepting said beam, and to transmit substantially all of the radiation from said source to said detector; and
   actuating means for moving said standardization means to enclosue said beam.

2. The apparatus of claim 1 further comprising:
   housing means for enclosing said standardization means and said beam, said housing means having at least two apertures permitting said gas particles to enter said means and to exit from said means.

3. The apparatus of claim 2 wherein said housing means is substantially tubular in shape and is hollow.

4. A method of measuring the amount of gas particles, using an apparatus having a source, capable of emitting a beam of radiation at a frequency which is absorbed by said gas particles; a detector; said beam aligned to impinge said detector and said gas particles; means positioned immediately adjacent to said beam, capable of being moved in a direction substantially perpendicular to said beam to enclose said beam, to prevent said gas particles from intercepting said beam, and to transmit substantially all of the radiation from said source to said detector; said method comprises:

emitting said beam of radiation at said frequency;

measuring the amount of radiation received by said detector;

moving said means in a direction substantially perpendicular to said beam to enclose said beam;

determining the amount of radiation received by said detector; and calculating the amount of gas based upon said amount of radiation measured and said amount of radiation detected.

5. The method of claim 4 wherein the calculating step is in accordance with Beer's law of $$C=(1/\mu L)\text{Ln}(I_1/I_3)$$

where C—concentration of gas; $\mu$—absorption coefficient; L—path length; $I_1$—amount of radiation detected; and $I_3$—amount of radiation received.

6. A method of standardizing an apparatus for measuring gas particles, said apparatus having a source, capable of emitting a beam of radiation at a first frequency which is absorbed by said gas particles and a second frequency which is not absorbed by said gas particles; a detector; said beam aligned to impinge said detector and said gas particles; means positioned immediately adjacent to said beam, capable of being moved in a direction substantially perpendicular to said beam to enclose said beam, to prevent said gas particles from intercepting said beam, and to transmit substantially all of the radiation from said source to said detector; said method comprises:

emitting said beam of radiation;

moving said means in a direction substantially perpendicular to said beam to enclose said beam;

measuring the amount of radiation at said first frequency received by said detector;

determining the amount of radiation at said second frequency received by said detector; and standardizing said apparatus based upon said first frequency measured and said second frequency determined.

7. The method of claim 6 wherein said standardizing step further comprises:

dividing the first frequency determined by the second frequency measured.

\* \* \* \* \*